US010967361B2

(12) United States Patent
Chen et al.

(10) Patent No.: US 10,967,361 B2
(45) Date of Patent: Apr. 6, 2021

(54) CARBON DOPED TIN DISULPHIDE AND METHODS FOR SYNTHESIZING THE SAME

(71) Applicants: ACADEMIA SINICA, Taipei (TW); National Taiwan University, Taipei (TW)

(72) Inventors: Kuei-Hsien Chen, Taipei (TW); Indrajit Shown, Taipei (TW); Wei-Fu Chen, Taipei (TW); Li-Chyong Chen Lin, Taipei (TW)

(73) Assignees: ACADEMIA SINICA, Taipei (TW); NATIONAL TAIWAN UNIVERSITY, Taipei (TW)

( * ) Notice: Subject to any disclaimer, the term of this patent is extended or adjusted under 35 U.S.C. 154(b) by 209 days.

(21) Appl. No.: 15/940,122

(22) Filed: Mar. 29, 2018

(65) Prior Publication Data

US 2018/0280942 A1    Oct. 4, 2018

Related U.S. Application Data

(60) Provisional application No. 62/479,462, filed on Mar. 31, 2017.

(51) Int. Cl.
*B01J 27/04* (2006.01)
*B01J 35/00* (2006.01)
(Continued)

(52) U.S. Cl.
CPC .............. *B01J 27/04* (2013.01); *B01J 19/127* (2013.01); *B01J 21/18* (2013.01); *B01J 23/14* (2013.01);
(Continued)

(58) Field of Classification Search
CPC . B01J 27/04; B01J 19/127; B01J 21/18; B01J 23/14; B01J 27/20; B01J 35/0013; B01J 35/002; B01J 35/004; B01J 35/026; B01J 35/08; B01J 37/033; B01J 37/10; B01J 37/346; B01J 2219/0875; B01J 2219/0892; B01J 2219/1203; C07C 1/02;
(Continued)

(56) References Cited

U.S. PATENT DOCUMENTS 3,623,865 A * 11/1971 Case ..................... G03C 1/73
430/17
2010/0213046 A1    8/2010 Grimes et al.
2013/0079577 A1 *  3/2013 Ingram .................. C01G 19/02
585/733

FOREIGN PATENT DOCUMENTS

CN        10 1609885    * 12/2009    .............. H01M 4/04
CN        10 5964276    *  9/2016    .............. B01J 27/04
(Continued)

OTHER PUBLICATIONS

Derwent abstract of CN 105964276 A (Year: 2016).*
(Continued)

*Primary Examiner* — Patricia L. Hailey
(74) *Attorney, Agent, or Firm* — Muncy, Geissler, Olds & Lowe, P.C.

(57) ABSTRACT

Disclosed herein are carbon doped tin disulphide (C—$SnS_2$) and other $SnS_2$ composites as visible light photocatalyst for $CO_2$ reduction to solar fuels. The in situ carbon doped $SnS_2$ photocatalyst provide higher efficiency than the undoped pure $SnS_2$. Also disclosed herein are methods for preparing the catalysts.

10 Claims, 12 Drawing Sheets

(51) Int. Cl.
| | |
|---|---|
| *B01J 35/08* | (2006.01) |
| *B01J 35/02* | (2006.01) |
| *B01J 37/10* | (2006.01) |
| *B01J 37/34* | (2006.01) |
| *B01J 19/12* | (2006.01) |
| *C01B 3/04* | (2006.01) |
| *C01B 13/02* | (2006.01) |
| *C07C 45/00* | (2006.01) |
| *C07C 1/02* | (2006.01) |
| *B01J 21/18* | (2006.01) |
| *C07C 29/159* | (2006.01) |
| *C07C 45/45* | (2006.01) |
| *B01J 27/20* | (2006.01) |
| *B01J 23/14* | (2006.01) |
| *B01J 37/03* | (2006.01) |
| *B01J 37/04* | (2006.01) |

(52) U.S. Cl.
CPC .............. *B01J 27/20* (2013.01); *B01J 35/002* (2013.01); *B01J 35/004* (2013.01); *B01J 35/0013* (2013.01); *B01J 35/026* (2013.01); *B01J 35/08* (2013.01); *B01J 37/033* (2013.01); *B01J 37/10* (2013.01); *B01J 37/346* (2013.01); *C01B 3/045* (2013.01); *C01B 13/0207* (2013.01); *C07C 1/02* (2013.01); *C07C 29/159* (2013.01); *C07C 45/00* (2013.01); *C07C 45/45* (2013.01); *B01J 37/04* (2013.01); *B01J 2219/0875* (2013.01); *B01J 2219/0892* (2013.01); *B01J 2219/1203* (2013.01); *C07C 2527/04* (2013.01)

(58) Field of Classification Search
CPC ....... C07C 29/159; C07C 45/00; C07C 45/45; C07C 2527/04; C01B 3/045; C01B 13/0207
USPC .......................................... 502/216, 220, 222
See application file for complete search history.

(56) References Cited

FOREIGN PATENT DOCUMENTS

| | | | | |
|---|---|---|---|---|
| CN | 10 9304187 | * | 2/2019 | ............. B01J 27/04 |
| FR | 3041960 | * | 4/2017 | ............. C07C 57/05 |
| WO | WO 2011/020825 A1 | | 2/2011 | |
| WO | WO2012/168355 A1 | | 12/2012 | |

OTHER PUBLICATIONS

Tadesse Billo et al., "A mechanistic study of molecular CO2 interaction and adsorption on carbon implanted SnS2 thin film for photocatalytic CO2 reduction activity." Nano Energy 72, pp. 1-10 (Year: 2020).*

Mohsen Cheraghizade et al., "The effect of tin sulfide quantum dots size on photocatalytic and photovoltaic performance." Materials Chemistry and Physics 195, pp. 187-194. (Year: 2017).*

Liu Han et al., "Nanoconnposites based on 3D macroporous biomass carbon with SnS2 nanosheets hierarchical structure for efficient removal of hexavalent chromium." Chemical Engineering Journal 369, pp. 1138-1149. (Year: 2019).*

Haifeng Xu et al., "Facile one-step synthesis of uniformly carbon-mixed tin sulfide hexagonal nanodisks as low-cost counter electrode material for dye-sensitized solar cells." Materials Letters 17, pp. 147-177. (Year: 2016).*

Inoue et al., "Photoelectrocatalytic reduction of carbon dioxide in aqueous suspensions of semiconductor powders", Nature vol. 277, Feb. 22, 1979, pp. 637-638.

Liu et al., "Tunable Photocatalytic Selectivity of Hollow TiO2 Microspheres Composed of Anatase Polyhedra with Exposed {001} Facets", J. Am. Chem. Soc., 2010, 132. (34), pp. 11914-11916.

Yi et al., "Titanium Dioxide-Based Nanomaterials for Photocatalytic Fuel Generations", Chem. Rev., 2014, 114 (19), pp: 9987-10043.

Navalon et al., "Photocatalytic $CO_2$ Reduction using Non-Titanium Metal Oxides and Sulfides", ChemSusChem 2013, 6, pp. 562-577.

Hsu et al., "Graphene oxide as a promising photocatalyst for $CO_2$ to methanol conversion", Nanoscale. Jan. 7, 2013;5(1): pp. 262-268.

Wang et al., "Sulfur-doped g-$C_{3N4}$ with enhanced photocatalytic $CO_2$-reduction performance", Applied Catalysis B: Environmental, vols. 176-177, Oct. 2015, pp. 44-52.

Tan et al., "Reduced graphene oxide-$TiO_2$ nanocomposite as a promising visible-light-active photocatalyst for the conversion of carbon dioxide", Nanoscale Research Letters 2013, 8:465, pp. 1-9.

Xiang et al., "Synergetic Effect of $MoS_2$ and Graphene as Cocatalysts for Enhanced Photocatalytic $H_2$ Production Activity of $TiO_2$ Nanoparticles", J. Am. Chem. Soc., 2012, 134 (15), pp. 6575-6578.

Shown et al., "Highly Efficient Visible Light Photocatalytic Reduction of $CO_2$ to Hydrocarbon Fuels by Cu-Nanoparticle Decorated Graphene Oxide", Nano Lett., 2014, 14 (11), pp. 6097-6103.

Zhang et al., "Metal sulphide semiconductors for photocatalytic hydrogen production", Catal. Sci. Technol., 2013,3, pp. 1672-1690.

Yang et al., "$SnS_2$ as low-cost counter-electrode materials for dye-sensitized solar cells", Materials Letters, vol. 133, Oct. 15, 2014, pp. 197-199.

Ou et al., "Physisorption-Based Charge Transfer in Two-Dimensional $SnS_2$ for Selective and Reversible $NO_2$ Gas Sensing", ACS Nano. Oct. 27, 2015;9(10): pp. 10313-10323.

Wang et al., "One-pot synthesis of 3D flower-like heterostructured $SnS_2/MoS_2$ for enhanced supercapacitor behavior", RSC Adv., 2015, 5, pp. 89069-89075.

Liu et al., "Evaluating Pristine and Modified $SnS_2$ as a Lithium-Ion Battery Anode: A First-Principles Study", ACS Appl. Mater. Interfaces, 2015, 7 (7), pp. 4000-4009.

Sun et al., "Visible-light photocatalytic reduction of carbon dioxide over $SnS_2$," Materials Letters, vol. 174, Jul. 1, 2016, pp. 238-241.

Shown et al., "Carbon-doped $SnS_2$ nanostructure as a high-efficiency solar fuel catalyst under visible light", Nature Communications vol. 9, Article No. 169 (2018) pp: 1-10.

* cited by examiner

CARBON DOPED TIN DISULPHIDE AND METHODS FOR SYNTHESIZING THE SAME

CROSS REFERENCE OF RELATED APPLICATIONS

This non-provisional application claims priority to U.S. provisional patent application Ser. No. 62/479,462 filed on Mar. 31, 2017. This and all other extrinsic materials discussed herein are hereby incorporated by reference in their entirety.

BACKGROUND

Technical Field

The present invention relates to the carbon doped $SnS_2$ and related $SnS_2$ composites as an efficient photocatalyst for conversion of carbon dioxide gas and water vapor to hydrocarbons (acetaldehyde, methanol etc) under visible light.

Related Art

The increasing demand of reduce fossil-fuel consumption, and renewable solar-energy generation processes are highly challenging global environmental energy issues. In particular, hydrocarbon's formation via photocatalytic carbon dioxide ($CO_2$) reduction under visible-light irradiation offers an attractive solution for solving simultaneously the incoming clean renewable energy and anthropogenic greenhouse emission problems. Since 1979, the pioneer demonstration of photocatalytic $CO_2$ reduction using various semiconductors the photocatalytic $CO_2$ reduction to solar fuels has attracted tremendous interest. (Inoue et al. Nature, 1979, 277, 637.) Over the years, many significant efforts have been applied to develop an efficient photocatalyst for the $CO_2$ reduction to hydrocarbons. Among the entire reported semiconductor photocatalyst, only $TiO_2$ and $TiO_2$ based composites are widely used for $CO_2$ photoreduction because of their comparatively low cost, low toxicity and photocorrosion resistance. (Liu et al. J. Am. Chem. Soc. 2010, 132, 11914, Yi et al. Chem. Rev. 2014, 114, 9987) However, wide band gap $TiO_2$ or other related wide band gap semiconductor photocatalysts are not enough to use for practical application due to their limited visible light absorption (Navalon et al. ChemSusChem 2013, 6, 562). On the other hand recent years, several carbonaceous hybrid materials GO (Hsu et al. Nanoscale, 2013, 5, 262.), g-C3N4 (Wang et al. Applied Catalysis B: Environmental, 2015, 176,44), $TiO_2$/rGO (Tan et al. Nanoscale Research Lett. 2013, 8, 465.), $MoS_2$/rGO (Xiang et al. J. Am. Chem. Soc. 2012, 134, 6575) and Cu-GO (Shown et al. Nano Lett. 2014, 14, 6097) have been reported as a promising photocatalyst for $CO_2$ reduction to solar fuels conversion. However, the $CO_2$ reduction process is more complicated multi-electron process and forming several hydrocarbon products. Thus, it is highly necessary to introduce a narrow bandgap nanostructure photocatalyst with suitable band structure to drive the $CO_2$ reduction process under visible light and forming selective hydrocarbons after multi-electron reduction. In addition, several narrow band gap metal sulfides such as CdS, PbS, CdSe, $MoS_2$ have been introduced as a photocatalyst or a co-catalyst together with another wide-band gap semiconductor for photocatalytic reaction under visible light (Zhang et al. Catal. Sci. Technol., 2013, 3, 1672.). Although CdS and PbS contains sufficient potential characteristics as a photocatalyst, however, they have less explored as a commercial photocatalyst due to the toxicity problem of Cd and Pb. Therefore, it's highly desirable to explore nontoxic narrow bandgap metal sulfide for photocatalytic $CO_2$ reduction. Among various metal sulfides, $SnS_2$ is one of the narrow bandgap nontoxic semiconductors associated with dichalcogenide family. Recently, it has been attracted for its potential applications as a light absorber layer for dye-sensitized solar cell (Yang et al. Materials Lett., 2014, 133, 197.), gas sensing (Ou et al. ACS Nano, 2015, 9, 10313), energy storage (Wang et al. RSC Adv., 2015, 5, 89069.) and conversion (Liu et al. ACS Appl. Mater. Interfaces, 2015, 7, 4000.). $SnS_2$ possesses $CdI_2$ crystal structure, consisting sandwiched S—Sn—S layers bounded by weak van der Waals's interaction. In the sandwiched structure tin cations are octahedrally coordinated by nearest six sulfur atoms. $SnS_2$ is an n-type semiconductor with a narrow bandgap around 2.2-2.4 eV at room temperature, and high quantum yield, thus it shows several benefits to be a good photocatalyst under visible light. Recently, Sun et al. have reported the photocatalytic $CO_2$ reduction to CO over $SnS_2$ (Sun et al. Materials Letters, 2016, 174, 238). However the overall photocatalytic performance is far low from the practical requirement due to the fast recombination of photogenerated charge carrier. To overcome this problem it is necessary to modify this semiconductor by doping it with metal or nonmetals. In semiconductors, doping with nonmetal carbonaceous materials is very popular in photocatalyst system due to their wide range of light absorption and low photo corrosion as compared with metal. The doped carbon acts as an excellent electron acceptor center and suppresses the charge recombination in the electron transfer process due to electronic interaction between doped carbon and the semiconductor. This doping process effectively improves the photocatalytic performance of the semiconductor.

SUMMARY

The present disclosure discloses a simple hydrothermally and microwave synthesized in situ carbon doped $SnS_2$ nanomaterials as a gas phase photocatalyst for the reduction of $CO_2$ with water vapor to produce hydrocarbons under visible light. The L-cysteine assisted hydrothermally synthesized carbon doped $SnS_2$ nanostructure has been selectively forming acetaldehyde with a conversion rate of around 28.6 µmole/hr·g under visible light. The thiourea assisted hydrothermally synthesized carbon doped $SnS_2$ nanostructure also has been used in the art to obtain a conversion rate of about 1.6 µmole/hr·g under visible light.

In general, the in situ carbon doped $SnS_2$ photocatalyst provided by this disclosure may be a mixture of $SnS/SnS_2$, $Sn_2S_3/SnS_2$ with different ratios and various nanostructures like sheet type, flower type, sphere type or needle shape.

In view of the foregoing objectives, the present disclosure discloses a photocatalyst based on in situ carbon doped tin disulfide nanostructure based on the chemical formula C—$SnS_x$, wherein $1.5 \leq x \leq 2$, with metal, metal oxide or other metal sulfide co-catalyst deposited on it. The co-catalyst may be selected from the following groups Ag, Cu, Au, Pt, Ni, Zn, $TiO_2$, ZnO, $WO_3$, $Cu_2O$, CuO, $SnO_2$, CdS, $MoS_2$, ZnS, NiS or mixture thereof.

In another aspect, preparing $SnS_2$-GO, $SnS_2$-rGO composites as a photocatalyst with mixture of graphene oxide or reduced graphene oxide together with $SnS_2$ by microwave or hydrothermal process.

In one embodiment, the photocatalyst is a mixture of $SnS/SnS_2$ or $Sn_2S_3/SnS_2$.

In one embodiment, the photocatalyst has a nanostructure which is selected from the group consisting of sheet type, flower type, sphere type, needle shape and a mixture thereof.

In one embodiment, the photocatalyst has a nanostructure with a dimension ranging from 3 to 300 nm in length and in diameter.

In one embodiment, the photocatalyst further comprises a co-catalyst which is selected from the group consisting of metal, metal oxide, and metal sulfide and a mixture thereof, and the co-catalyst is deposited on the carbon doped tin sulfide.

In one embodiment, in the photocatalyst, contents of Sn, S and C are 29.49-37.23, 55.32-57.69 and 7.45-12.82 atomic %, respectively.

In one embodiment, the photocatalyst is $SnS_{1.95}C_{0.43}$ or $SnS_{1.49}C_{0.2}$.

In view of the foregoing objectives, the disclosure also provides a carbon doped tin disulphide ($C-SnS_2$) which comprises a sheet-structured $SnS_2$ of nanometer scale.

In one embodiment, the carbon doped tin disulphide has a size of 3-300 nm.

In one embodiment, the carbon doped tin disulphide has a carbon content ranging from 0.5% to 20%.

In one embodiment, the carbon doped tin disulphide has a signature peak at 312 $cm^{-1}$ in Raman spectra.

In one embodiment, the carbon doped tin disulphide has a bandgap ranging from 2.0-2.5 eV.

In view of the foregoing objectives, the disclosure further provides a method for synthesizing the aforementioned carbon doped tin disulphide. The method comprises the following steps of: mixing $SnCl_4.5H_2O$ and L-cysteine ($C_3H_7NO_2S$) into distilled water; and allowing $SnCl_4.5H_2O$ and L-cysteine ($C_3H_7NO_2S$) to react under hydrothermal or microwave reactor to form a $C-SnS_2(C)$ nanostructured photocatalyst.

In one embodiment, the photocatalyst is prepared by a hydrothermal method with L-cysteine.

In one embodiment, the $C-SnS_2(C)$ is prepared to form nanoflower morphology.

In one embodiment, the photocatalyst contains $SnS_2$ polycrystalline phases dominated by 001, 100, 101 and 110.

In one embodiment, in the photocatalyst, contents of Sn, S and C of the photocatalyst are 29.49, 57.69 and 12.82 atomic %, respectively.

In one embodiment, the photocatalyst is $SnS_{1.95}C_{0.43}$.

In view of the foregoing objectives, the disclosure further provides a method for synthesizing the aforementioned carbon doped tin disulphide, and the method comprises the following steps of: mixing $SnCl_4.5H_2O$ and thiourea ($CH_4N_2S$) into PEG-400, and allowing $SnCl_4.5H_2O$ and thiourea ($CH_4N_2S$) to react under hydrothermal or microwave reactor to form a $C-SnS_2(T)$ nanostructured photocatalyst.

In one embodiment, the $C-SnS_2(T)$ is prepared with nanocage morphology.

In one embodiment, the photocatalyst contains $SnS_2$ polycrystalline phases dominating 001, 100, 101 and 110.

In one embodiment, the $C-SnS_2(T)$ nanostructured photocatalyst is composed of several thin $SnS_2$ nano sheets having 1 to 2 μm.

In one embodiment, the $C-SnS_2(T)$ nanostructured photocatalyst is composed of Sn, S and C around 37.23, 55.32 and 7.45 atomic %, respectively.

In one embodiment, the $C-SnS_2(T)$ nanostructured photocatalyst is $SnS_{1.49}C_{0.2}$.

In view of the foregoing objectives, the disclosure further provides a method for producing a solar fuel, comprising the following steps: reducing gas phase $CO_2$ or splitting water with any one of the aforementioned photocatalysts.

In one embodiment, the reduction of $CO_2$ or splitting of water is carried out under visible light.

In one embodiment, the solar fuel is a hydrocarbon which is selected from the group consisting of acetaldehyde, methanol, ethanol and a mixture thereof.

In one embodiment, the photocatalyst has a maximum solar fuel production rate of 1.6-28.6 $\mu mole/g_{cat}$, hr.

In one embodiment, the solar fuel is hydrogen and oxygen.

Accordingly, the photocatalyst, the carbon doped tin disulphide ($C-SnS_2$), the method for synthesizing the aforementioned carbon doped tin disulphide, and method for producing a solar fuel, are provided by the present disclosure. Solar fuels can be generated from the reduction of $CO_2$ under visible light on the surface of carbon doped $SnS_2$ photocatalyst. Also, the in situ carbon doped $SnS_2$ photocatalyst is prepared in an environmentally friendly and energy-efficient manner from nontoxic materials. To the best of our knowledge, this study is the first to describe in situ carbon doped $SnS_2$ nanostructures and related composites for photocatalytic $CO_2$ reduction application under visible-light irradiation. The in situ carbon doped $SnS_2$ absorbs visible light to generate an electron-hole pair, and interspatial doped carbon suppresses the charge recombination process. The photogenerated electrons and holes would migrate to $SnS_2$ surface and serve as a reducing and oxidizing sites for $CO_2$ reduction to hydrocarbon and water oxidation to oxygen formation. The present disclosure addresses the simple hydrothermally synthesized in situ carbon doped $SnS_2$ nanostructure, thin film, nanoparticles as a potential photocatalyst for gas-phase photochemical reduction of $CO_2$ to hydrocarbon fuels such as acetaldehyde as major product under visible light.

BRIEF DESCRIPTION OF THE DRAWINGS

The embodiments will become more fully understood from the detailed description and accompanying drawings, which are given for illustration only, and thus are not limitative of the present invention, and wherein.

DETAILED DESCRIPTION OF THE INVENTION

Figure 1:
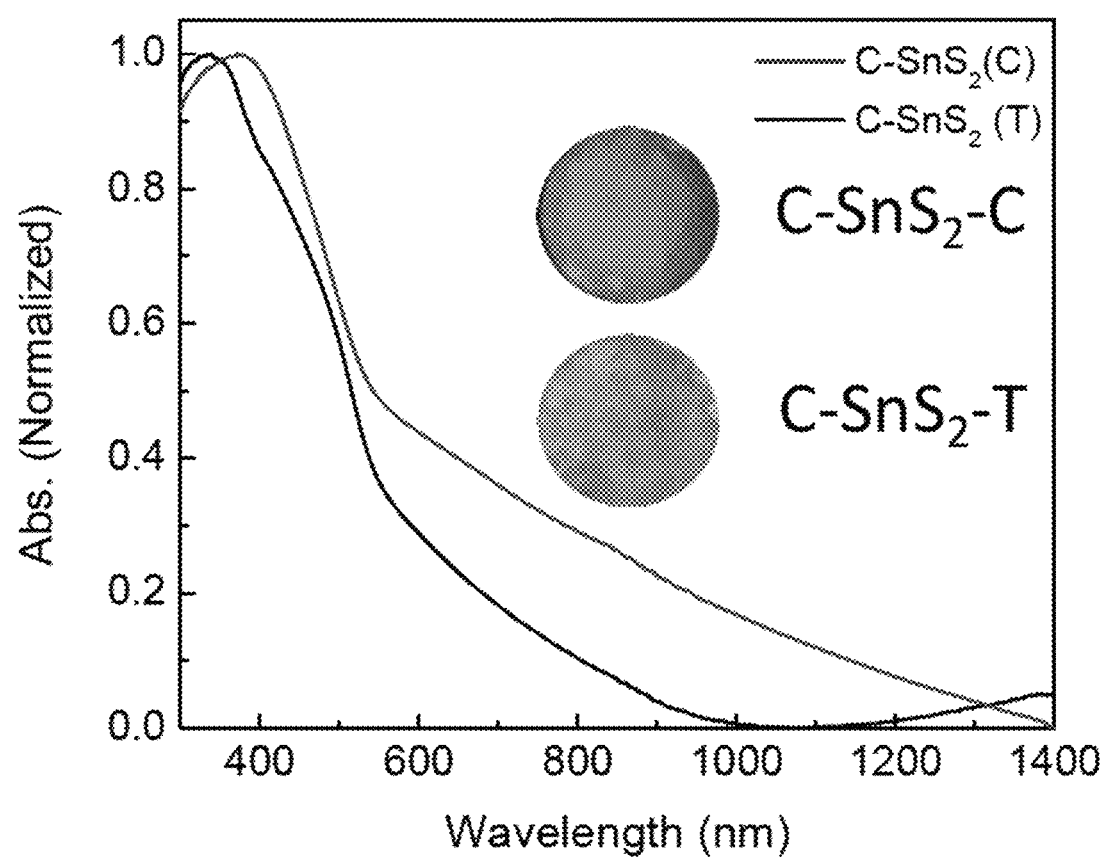
FIG. 1 Absorption spectra of the $C-SnS_2(C)$ and $C-SnS_2(T)$ obtained by the hydrothermal method of the present invention.

The embodiments of the invention will be apparent from the following detailed description, which proceeds with reference to the accompanying drawings, wherein the same references relate to the same elements.

Photocatalyst of Carbon Doped Tin Sulfide (C—SnS$_x$)

According to one embodiment of the present disclosure, a photocatalyst comprises a carbon doped tin sulfide. The carbon doped tin sulfide is represented by a formula of C—SnS$_x$, wherein 1.5≤x≤2. The photocatalyst has a nanostructure which is sheet type, flower type, sphere type, needle shape or a mixture thereof, and the dimension of the photocatalyst ranges from 3 to 300 nm in length and in diameter. The tin sulfide part of the photocatalyst can be a mixture of SnS/SnS$_2$ or Sn$_2$S$_3$/SnS$_2$. Moreover, in the photocatalyst, contents of Sn, S and C may be 29.49-37.23, 55.32-57.69 and 7.45-12.82 atomic %, respectively. For some specific examples, the photocatalyst can be SnS$_{1.95}$C$_{0.43}$ or SnS$_{1.49}$C$_{0.2}$.

Alternatively, the photocatalyst may further comprise a co-catalyst which is metal, metal oxide, metal sulfide or a mixture thereof, and the co-catalyst is deposited on the carbon doped tin sulfide. For example, the co-catalyst can be Ag, Cu, Au, Pt, Ni, Zn, TiO$_2$, ZnO, WO$_3$, Cu$_2$O, CuO, SnO$_2$, CdS, MoS$_2$, ZnS, NiS, or a mixture thereof.

According to another embodiment of the present disclosure, the carbon doped tin sulfide of the photocatalyst is carbon doped tin disulphide (C—SnS$_2$) and the carbon doped tin disulphide comprises a sheet-structured SnS$_2$ of nanometer scale. Similarly, the carbon doped tin disulphide may have a size ranging from 3-300 nm. In this embodiment, the carbon doped tin disulphide has a carbon content ranging from 0.5% to 20%, and has a signature peak at 312 cm$^{-1}$ in Raman spectra. Also, the bandgap of the carbon doped tin disulphide may range from 2.0-2.5 eV.

Method for Synthesizing Carbon Doped Tin Disulphides: C—SnS$_2$(C) and C—SnS$_2$(T)

According to further another embodiment of the present disclosure, a method for synthesizing the aforementioned carbon doped tin disulphide by a hydrothermal method with L-cysteine (such carbon doped tin disulphide is abbreviated as "C—SnS$_2$(C)" herein) is provided. The method comprises the following steps of: mixing SnCl$_4$.5H$_2$O and L-cysteine (C$_3$H$_7$NO$_2$S) into distilled water; and allowing SnCl$_4$.5H$_2$O and L-cysteine (C$_3$H$_7$NO$_2$S) to react under hydrothermal or microwave reactor to form a C—SnS$_2$(C) nanostructured photocatalyst. The C—SnS$_2$(C) prepared by such synthetic method may form a nanoflower morphology. The C—SnS$_2$(C) nanostructured photocatalyst contains SnS$_2$ polycrystalline phases dominated by 001, 100, 101 and 110. In the C—SnS$_2$(C) nanostructured photocatalyst, contents of Sn, S and C of such photocatalyst are 29.49, 57.69 and 12.82 atomic %, respectively. For a specific example, the C—SnS$_2$(C) nanostructured photocatalyst is SnS$_{1.95}$C$_{0.43}$.

Alternatively, the disclosure further provides a method for synthesizing the aforementioned carbon doped tin disulphide with thiourea (such carbon doped tin disulphide is abbreviated as "C—SnS$_2$(T)" herein), and the method comprises the following steps of: mixing SnCl$_4$.5H$_2$O and thiourea (CH$_4$N$_2$S) into PEG-400, and allowing SnCl$_4$.5H$_2$O and thiourea (CH$_4$N$_2$S) to react under hydrothermal or microwave reactor to form a C—SnS$_2$(T) nanostructured photocatalyst. The C—SnS$_2$(T) prepared by such synthetic method may have a nanocage morphology. The C—SnS$_2$(T) nanostructured photocatalyst contains SnS$_2$ polycrystalline phases dominating 001, 100, 101 and 110. The C—SnS$_2$(T) nanostructured photocatalyst can be composed of several thin SnS$_2$ nano sheets having 1 to 2 μm. Moreover, the C—SnS$_2$(T) nanostructured photocatalyst is composed of Sn, S and C around 37.23, 55.32 and 7.45 atomic %, respectively. For a specific example, the C—SnS$_2$(T) nanostructured photocatalyst is SnS$_{1.49}$C$_{0.2}$.

Method for Producing Solar Fuel

According to still another embodiment of the present disclosure, the invention further provides a method for producing a solar fuel, comprising the following steps: reducing gas phase CO$_2$ or splitting water with any one of the aforementioned photocatalysts. In the present embodiment, the reduction of CO$_2$ or splitting of water can be carried out under visible light. The solar fuel may be hydrogen and oxygen, or a hydrocarbon which is acetaldehyde, methanol, ethanol or a mixture thereof. The maximum solar fuel production rate of the photocatalyst used in the present embodiment ranges from 1.6 to 28.6 μmole/g$_{cat}$, hr.

To illustrate some characteristics of aforementioned embodiments, such as, but not limited to, the synthesis of carbon doped SnS$_2$, and the optical properties, morphology, microstructures, and photochemical CO$_2$ reduction activities of such carbon doped SnS$_2$ photocatalyst, there are several examples shown below.

EXAMPLE 1

Synthesis of Carbon Doped SnS$_2$ by Hydrothermal Process Based on Cystine [C—SnS$_2$(C)]

In a typical procedure, 1 mM of tin (IV) chloride pentahydrate (SnCl$_4$.5H$_2$O) and 5 mM L-cysteine (C$_3$H$_7$NO$_2$S) were added to a 60 ml of distilled water and gradually dispersed to form a homogeneous solution by vigorous magnetic stirring for 1 hr. at room temperature. Finally, the resulting solution was transferred into a Teflon-lined stainless autoclave. The autoclave was sealed and heated at 180° C. for 24 hrs. After hydrothermal reaction, the sample was cooled to room temperature naturally. The resulting product was collected by centrifugation at 8000 rpm for 10 min and washed several times with distilled water. Finally, the collected yellow C—SnS$_2$ powder was vacuum-dried at 80° C. overnight.

EXAMPLE 2

Synthesis of Carbon Doped $SnS_2$ by Hydrothermal Process Based on Thiourea [C—$SnS_2$(T)]

In a typical procedure, 1 mM of tin (IV) chloride pentahydrate ($SnCl_4 \cdot 5H_2O$) and 5 mM thiourea ($CH_4N_2S$) were added to a 60 ml of polyethylene glycol-400 (PEG-400) and gradually dispersed to form a homogeneous solution by vigorous magnetic stirring for 3 hr. at room temperature. Finally, the resulting solution was transferred into a Teflon-lined stainless autoclave. The autoclave was sealed and heated at 220° C. for 15 hrs. After hydrothermal reaction, the sample was cooled to room temperature naturally. The resulting product was collected by centrifugation at 8000 rpm for 10 min and washed several times with distilled water. Finally, the collected yellow C—$SnS_2$ powder was vacuum-dried at 80° C. overnight.

EXAMPLE 3

Characterization

The ultraviolet-visible absorption spectrum of powder samples was measured with a Jasco V-670 spectrophotometer using an integrated sphere. The crystal structures were determined by XRD using CuKα radiation (Bruker, D2 PHASER with XFlash). The surface morphology of all samples was characterized by field emission scanning electron microscopy (FESEM, JEOL, 6700F). The high-resolution transmission electron microscopy (HRTEM, JEOL-2100) studies with selected area electron diffraction (SAED) and EDX were also performed to determine morphology, crystal phase and elemental compositions. X-ray Photoelectron spectroscopy (XPS) analysis was performed on a theta probe ESCA VG Scientific (2002) using a monochromatic AlKa as the exciting source. The peak positions of the XPS were calibrated carefully with respect to the Au 4f peak. Finally, the XPS spectra were deconvoluted by using Voigt fitting function after a Shirley background subtraction procedure.

EXAMPLE 4

Photochemical $CO_2$ Reduction Experiment

Figure 9:
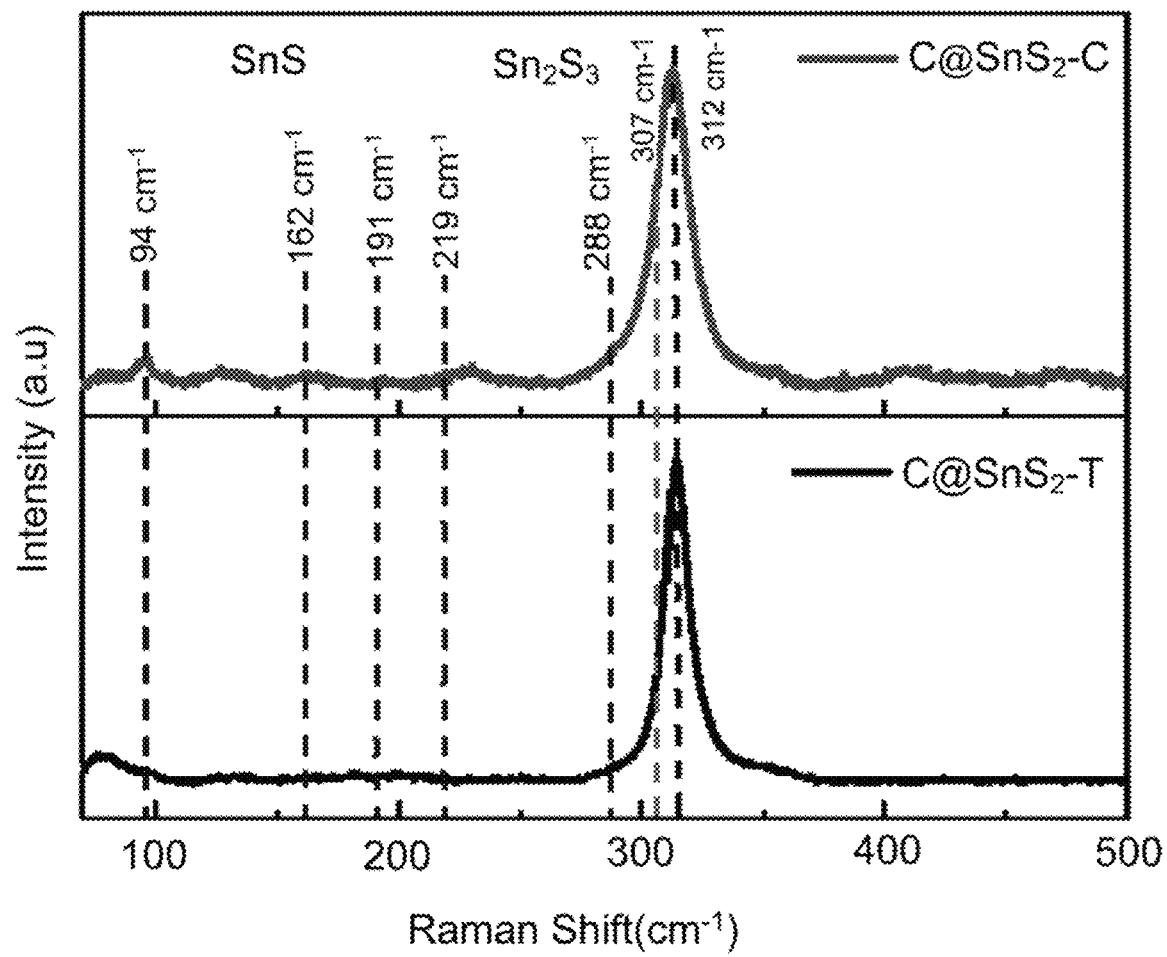
FIG. 9 Raman spectra of the C—SnS$_2$(C) and C—SnS$_2$(T).

The photocatalytic experiment for the reduction of $CO_2$ was performed at ambient temperature (25±5° C.) in a continuous gas flow reactor. The volume of the cylindrical reactor which was made of stainless steel and covered with Quartz-Glass was 300 ml (11 cm×4 cm). One sample dish containing 0.1 g of the photocatalysts obtained by the method of the present invention was placed in the middle of the reactor. A 300 W commercial halogen lamp was used as the simulated solar-light source. The lamp was vertically placed outside the reactor above the sample dish. Two mini fans were fixed around the lamp to avoid the temperature rise of the flow system. The catalyst powder spread onto the glass disc, with a diameter of around 4 cm. Initially nitrogen gas was purged inside the reactor to remove the air with other gases. After that $CO_2$ was purged inside the reactor for another 1 hour and control the flow rate at 4 sccm. The $CO_2$ was flowing through water to control the desire humidity level for entire experiment. The halogen lamp was turned on after one hour while adsorptions desorption of gas and photocatalyst reached the equilibrium. The concentration of methanol was continuously measured by a GC-FID in vapor phase. The detail schematic drawing of the experimental setup is shown in FIG. 9.

EXAMPLE 5

Optical Property of $SnS_2$ Photocatalyst

Figure 2:
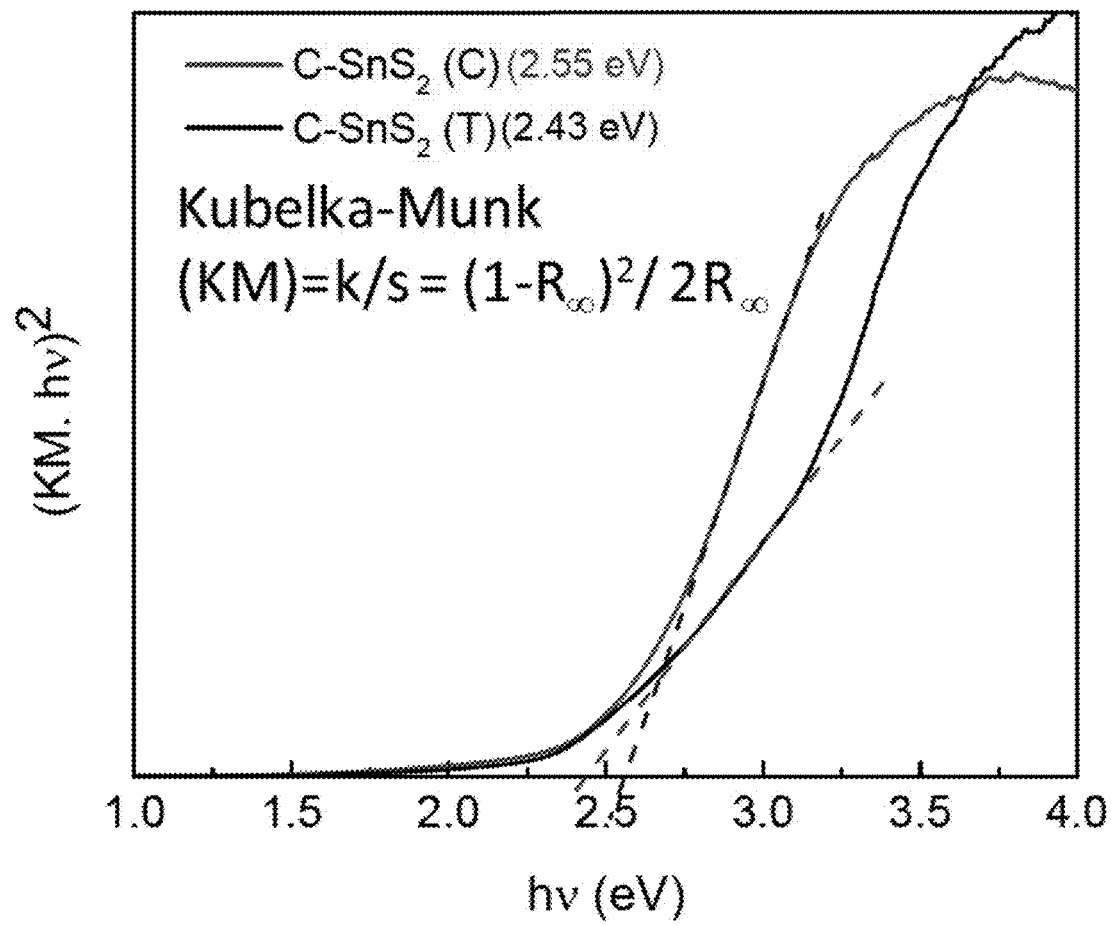
FIG. 2 Tauc plot and band gap calculation of the $C-SnS_2(C)$ and $C-SnS_2(T)$ obtained by the hydrothermal method of the present invention.

The UV-vis absorption spectra were performed to determine the optical absorption of the carbon doped $SnS_2$ photocatalyst prepared in example 1 and 2 respectively. As shown in FIG. 1, C—$SnS_2$(C) and C—$SnS_2$(T) present strong intense absorption band from UV to visible region around 300 to 550 nm. From the tauc plot in the FIG. 2, approximate bandgaps of 2.55 and 2.43 eV for C—$SnS_2$(C) and C—$SnS_2$(T), respectively, were obtained. It is observed that the narrow bandgap of the carbon doped $SnS_2$ photocatalyst provides excellent visible light responsive photocatalytic activity.

EXAMPLE 6

Structure of Carbon Doped $SnS_2$ Photocatalyst

Figure 3:
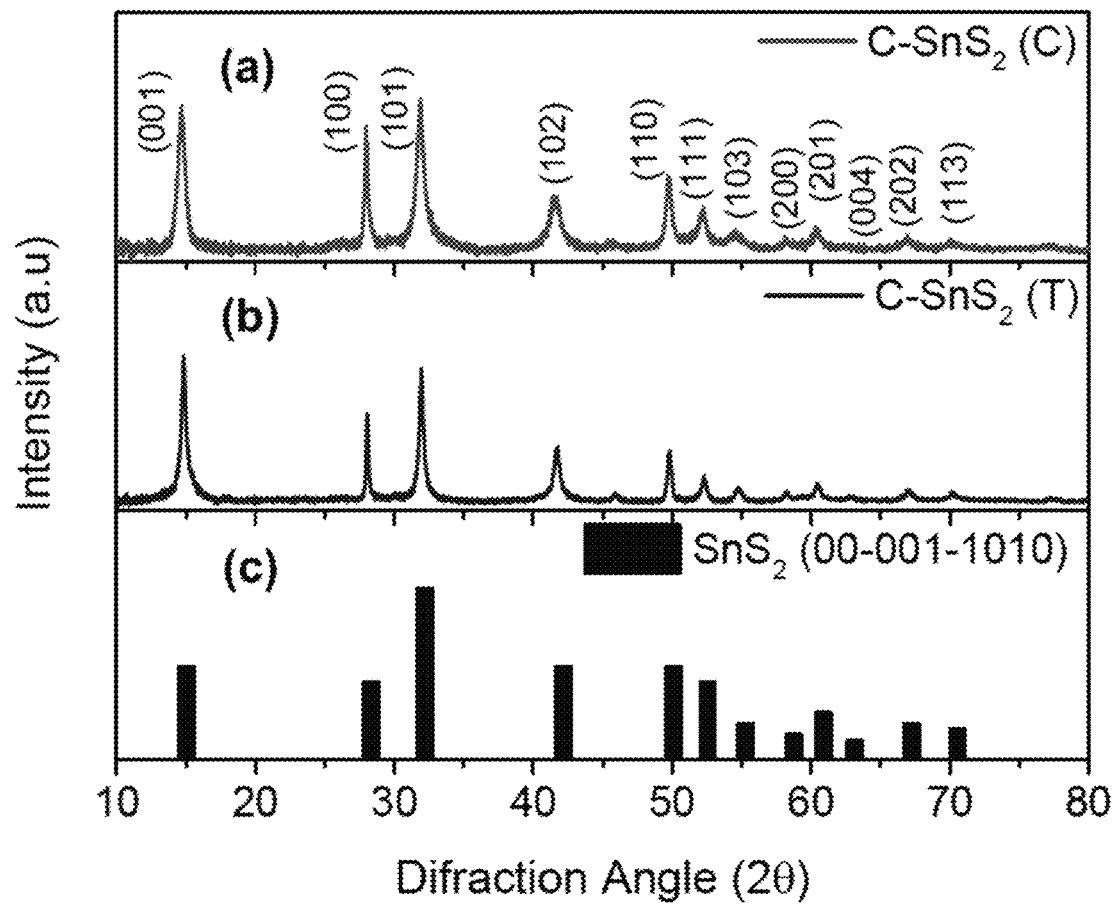
FIG. 3 Powder XRD pattern of the obtained (a) $C-SnS_2(C)$ and (b) $C-SnS_2(T)$ by the hydrothermal method of the present invention.

The crystal structure and phase composition of the as prepared carbon doped $SnS_2$ were characterized by XRD. Displayed in FIG. 3 are the X-ray diffraction (XRD) patterns of the as prepared C—$SnS_2$(C) and C—$SnS_2$(T) nanostructures photocatalyst in example 1 and 2. All the peaks in FIGS. 3a and b are indexed to the standard diffraction data of hexagonal $SnS_2$, which well match the literature values (JCPDS no 00-001-1010). The strong reflection and no impurity peak reveal the high purity and crystallinity of the as prepared samples. We observed the peak shifting slightly lower 2θ position which is due to crystal lattice expansion of $SnS_2$ by the interstitial doping of carbon in layer $SnS_2$. The (001) facet of the hexagonal $SnS_2$ shows quite strong intensity compared with standard value, which demonstrates that (001) orientation is preferentially oriented.

EXAMPLE 7

Morphology and Microstructure of $SnS_2$ Photocatalyst

Figure 4:
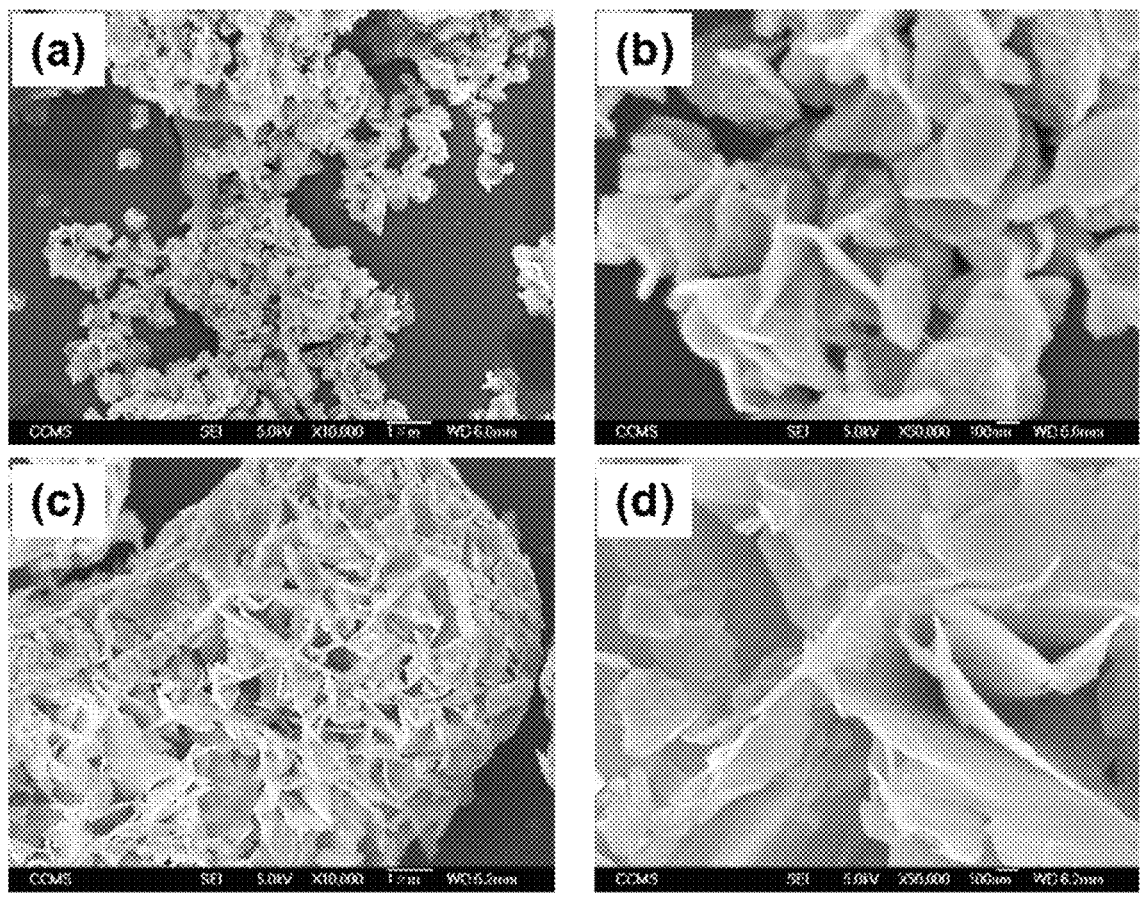
FIG. 4 SEM images of the (a-b) $C-SnS_2(C)$ and (c-d) $C-SnS_2(T)$ obtained by the hydrothermal method of the present invention.
Figure 5:
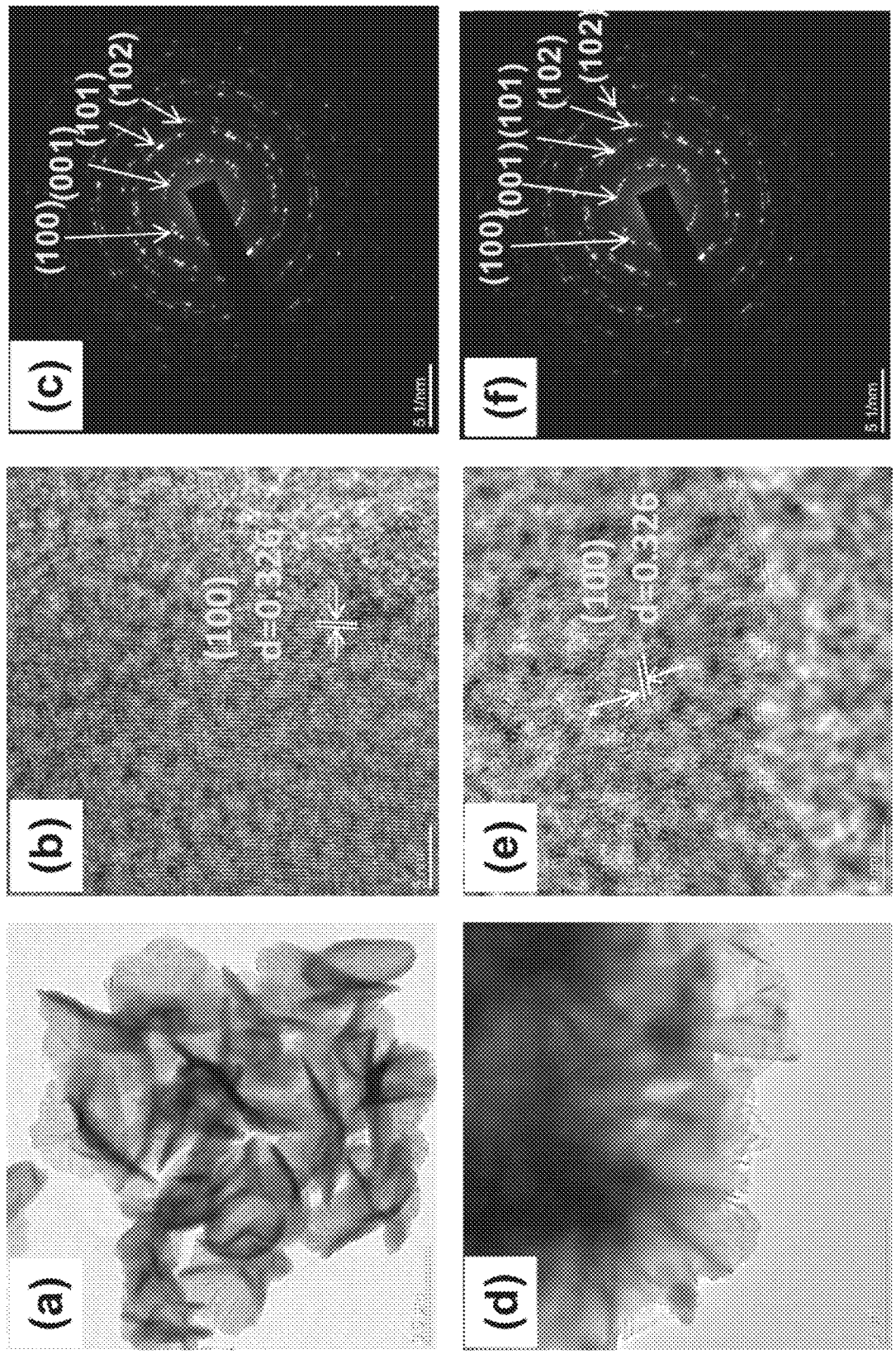
FIG. 5 HRTEM images of the (a-b) $C-SnS_2(C)$ and (d-e) $C-SnS_2(T)$ obtained by the hydrothermal method of the present invention. SAED pattern of the (c) $C-SnS_2(C)$ and (f) $C-SnS_2(T)$ obtained by the hydrothermal method of the present invention.

The morphology of the as prepared $SnS_2$ samples was characterized by FESEM. FIGS. 4(a, b) and 4(c, d) show the typical SEM images of C—$SnS_2$(C) and C—$SnS_2$(T) at low magnification and high magnification, respectively. C—$SnS_2$(C) clearly shows small flower type nanostructure formation with number of nanosheets with a uniform dimension around 300 to 400 nm length and diameter. The high resolution image clearly shows that several nanosheets with rough surface forming the nanoflower morphology. In the C—$SnS_2$(T) sample we observed nanosheet-interconnected cage type nanostructure, where nanosheets are thin and bigger than the C—$SnS_2$(C). The higher magnification of C—$SnS_2$(T) in FIG. 4d clearly shows the nanosheets are around micron size, thinner and with smooth surface morphology. Additionally, to investigate the more details morphology and structure features analysis of C—$SnS_2$(C) and C—$SnS_2$(T) samples, HRTEM and SAED were also performed as shown in FIG. 5. FIGS. 5(a, b) shows the microstructure of the C—$SnS_2$(C), its clearly observed that several thicker nanosheets are forming small nanoflower architecture showing clear lattice space around 0.326 nm which is corresponding to the interspacing of 001 planes of SnS$_2$. Moreover, C—SnS$_2$(T) shows that several thinner nanosheets forming a bigger interconnected nanocage microstructure with lattice spacing of the 001 plane at around 0.326 nm. In addition the corresponding SAED was performed for both the samples as shown in FIGS. 5c and f. The SAED of both samples reveal the polycrystalline and dominating 001, 100, 101 and 110 facets. This result is well consistent with the XRD analysis results.

EXAMPLE 8

Chemical Composition and Raman Spectrum of SnS$_2$ Photocatalyst

Figure 6:
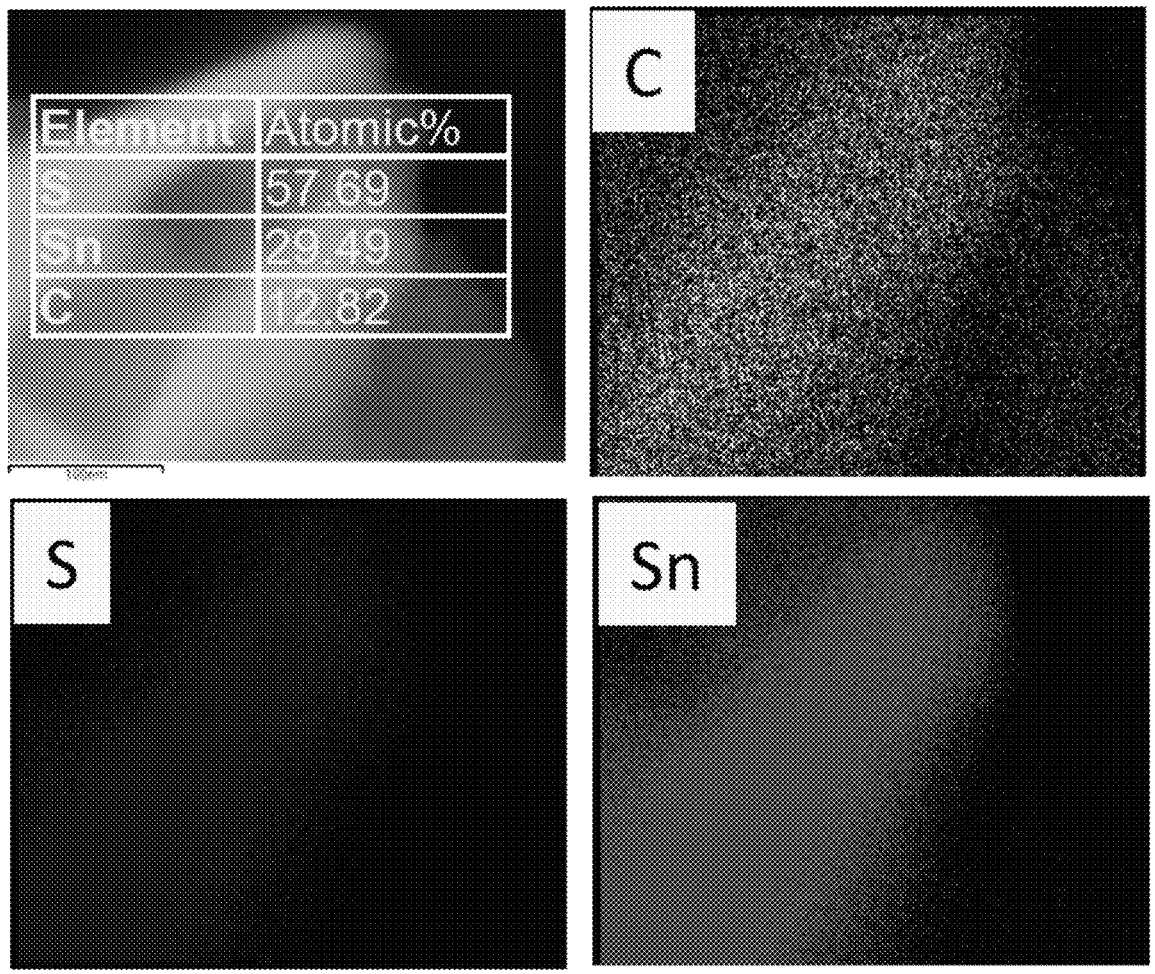
FIG. 6 TEM EDX elemental composition and elemental mapping of $C-SnS_2(C)$.
Figure 7:
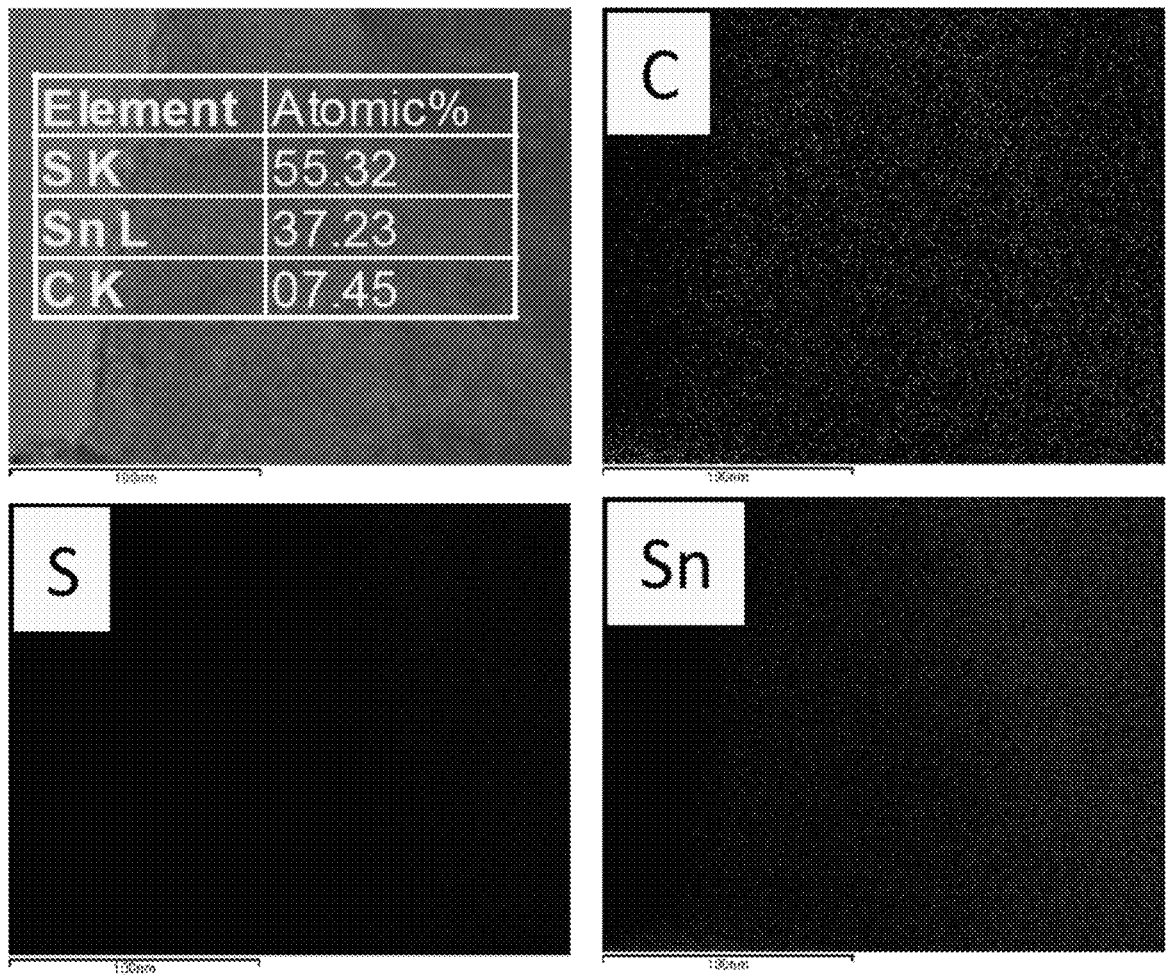
FIG. 7 TEM EDX elemental composition and elemental mapping of $C-SnS_2(T)$.
Figure 8:
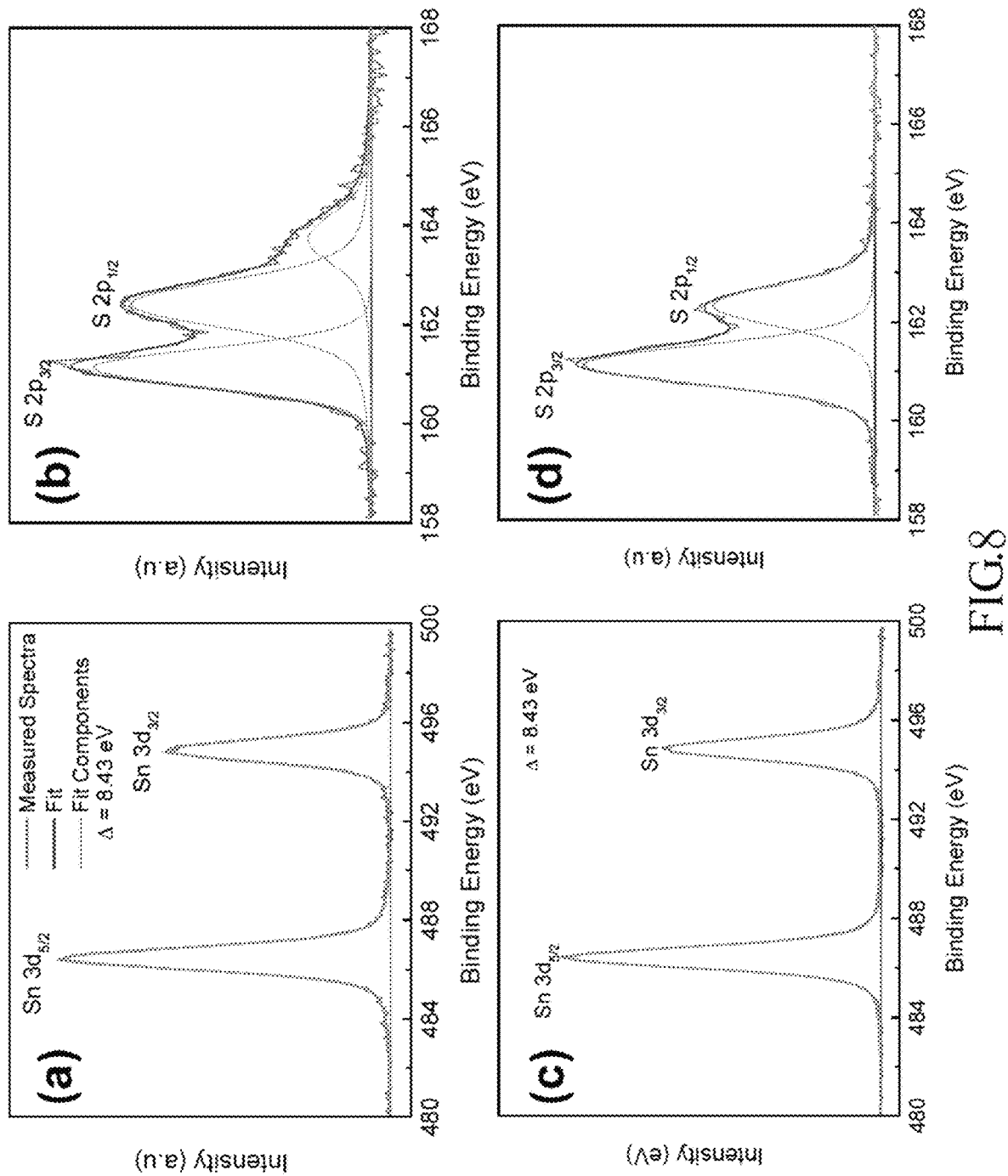
FIG. 8 High resolution XPS spectra of the Sn 3d and the S 2p of the (a-b) $C-SnS_2(C)$ and (c-d) $C-SnS_2(T)$ obtained by the method of the present invention.

The energy dispersive X-ray (EDX) spectra confirm the presence of Sn, S and C elements. The synthesized in situ carbon doped SnS$_2$ are denoted as C—SnS$_2$(C) and C—SnS$_2$(T), with measured C loading of 12.82 and 7.45 atomic % respectively. The observed Sn:S ratio for C—SnS$_2$(C) and C—SnS$_2$(T) are 1:1.95 and 1:1.5. FIGS. 6 and 7 show the STEM EDX elemental maps of the C—SnS$_2$ samples signifying that the Sn, S and C are evenly distributed within the SnS$_2$ nanostructure. FIG. 8 presents the comparison of high-resolution XPS spectra of Sn 3d and S 2p of the as prepared SnS$_2$—C and SnS$_2$-T samples. In FIGS. 8a and 8c, the measured binding energies corresponding to Sn 3d$_{5/2}$ and Sn 3d$_{3/2}$ are around 486.7 and 495.2 eV, respectively; these binding energies indicate Sn$^{4+}$ ions in SnS$_2$ samples. The difference at around 8.4 eV between the two strong Sn 3d peaks is characteristic of tetravalent Sn 3d states. Furthermore, in FIGS. 8b and 8d, the high resolution S 2p core level analysis at binding energies of around 162.8 and 164.0 eV correspond to S 2p$_{3/2}$ and S 2p$_{1/2}$, which are typical values for metal sulfide. The observed XPS binding energies of Sn 3d and S 2p spectra confirmed the Sn$^{4+}$ and S$^{2+}$ of as prepared SnS$_2$ samples. The Raman spectra of C—SnS$_2$(C) and C—SnS$_2$(T) are shown in FIG. 9 with signature peak at 312 cm$^{-1}$.

EXAMPLE 9

Photocatalytic CO$_2$ Reduction Activity of SnS$_2$ Photocatalyst

Figure 10:
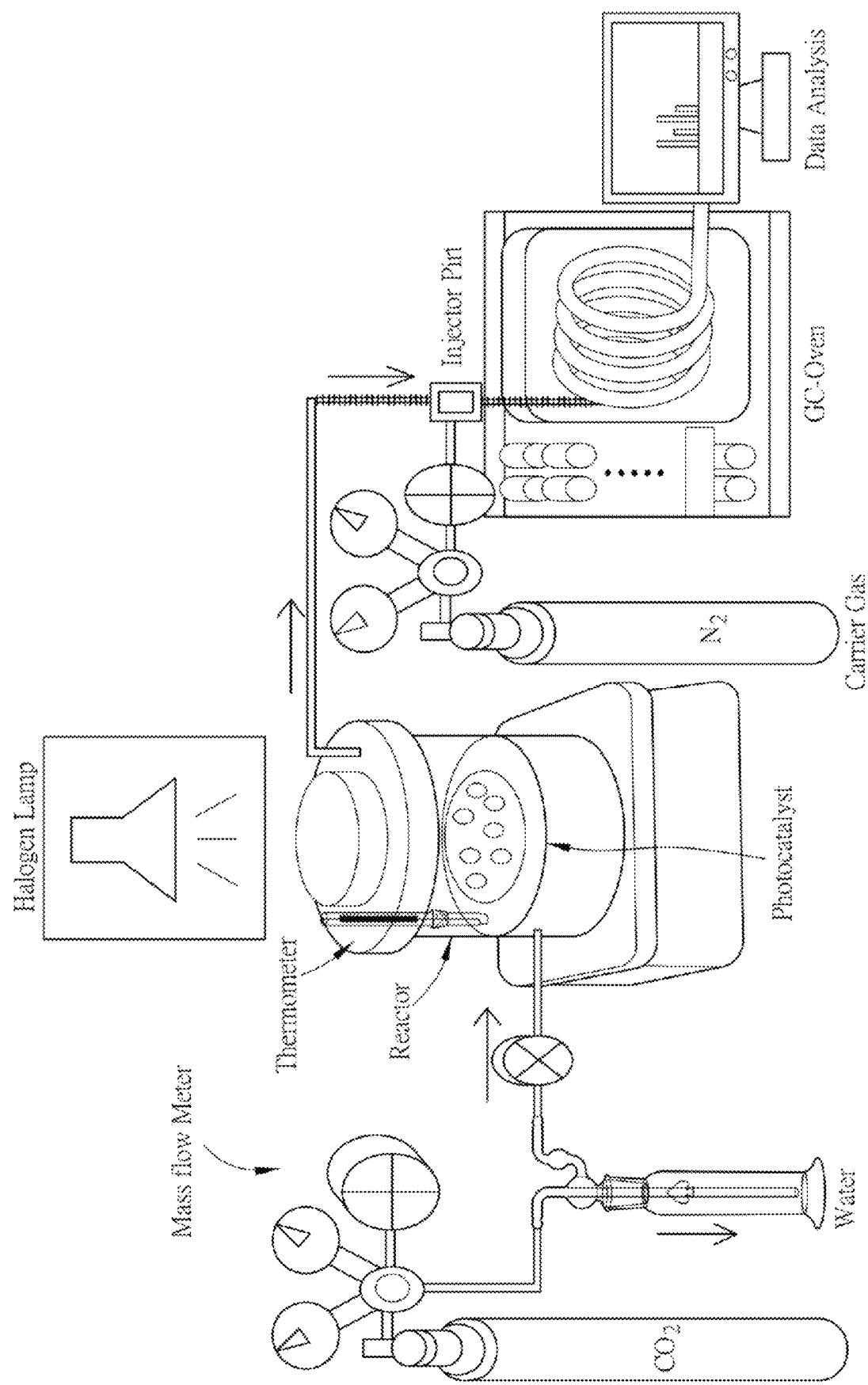
FIG. 10 The schematic diagram of the photocatalytic reduction of CO$_2$ with the photocatalysts via hydrothermal method of the present invention.
Figure 11:
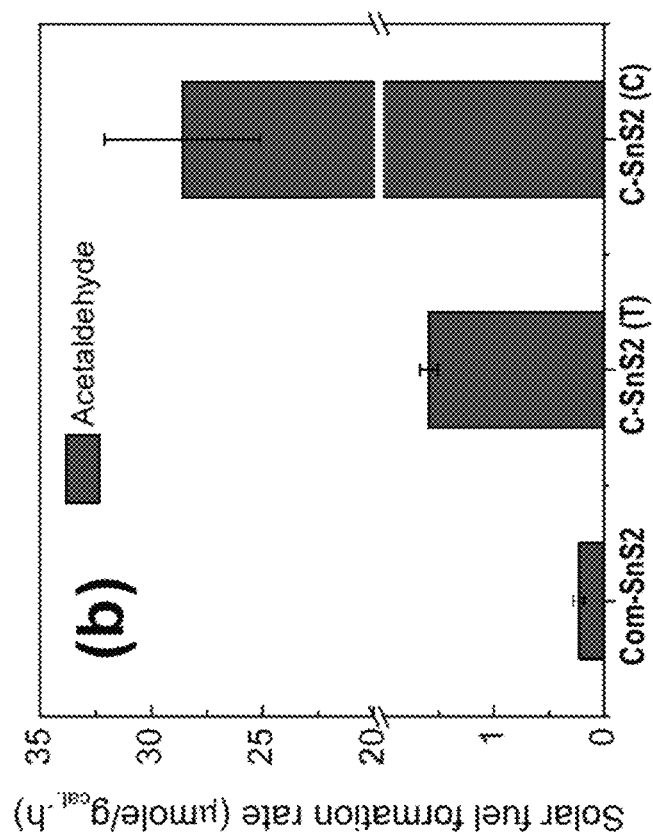
FIG. 11 CO$_2$ photoreduction analysis of the photocatalysts obtained by the method of the present invention and representative (a) cumulative acetaldehyde yields for C—SnS$_2$(C), C—SnS$_2$(T) and (b) acetaldehyde yield comparison for synthesized C—SnS$_2$(C) C—SnS$_2$(T) and commercial SnS$_2$ respectively.
Figure 11:
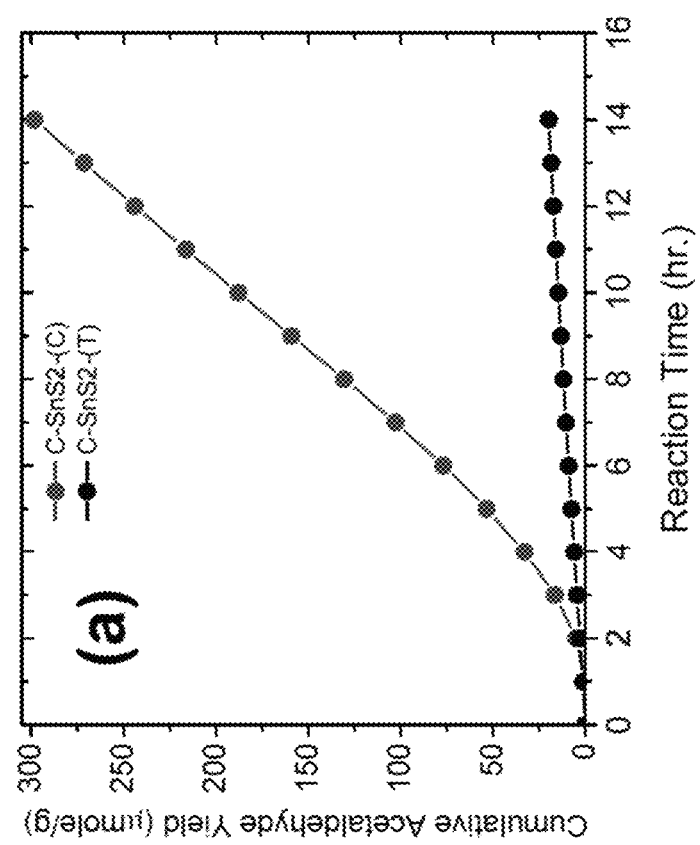

Photoreaction characteristics of the C—SnS$_2$(C) and C—SnS$_2$(T) nanostructures photocatalyst prepared in example 1 and 2 were determined through reaction of CO$_2$ and water in gas phase to produce hydrocarbons as indicated in the schematic in FIG. 10. The products of the CO$_2$ reduction are shown in FIG. 11. FIG. 11a illustrates the cumulative acetaldehyde production yield after 14 hours for the C—SnS$_2$(C) and C—SnS$_2$(T) nanostructures photocatalyst. The observed maximum cumulative acetaldehyde yields after 14 hours are 298.3 μmole/g$_{cat}$ and 19.9 μmole/g$_{cat}$ for C—SnS$_2$(C) and C—SnS$_2$(T) photocatalyst respectively. It can be seen that the prepared SnS$_2$ nanostructure photocatalyst exhibited clear photocatalytic CO$_2$ reduction activity under visible light and produced selective acetaldehyde as a major product under multi-electron reduction. Additionally, FIG. 11b shows a comparison of visible light photocatalytic CO$_2$ reduction to solar fuel formation rates of commercial SnS$_2$, C—SnS$_2$(T) and C—SnS$_2$(C). The maximum solar fuels formation rates for the commercial SnS$_2$, C—SnS$_2$(T) and C—SnS$_2$(C) photocatalyst are around 0.23±0.05, 1.69±0.08 and 28.6±3.5 μmole/g$_{cat}$, hr. In the in situ carbon doped SnS$_2$ the solar fuel formation rate was increased. The solar fuel formation rate was achieved at the highest value of around 28.6 μmole/g$_{cat}$, hr. for C—SnS$_2$(C). The photocatalytic solar fuel formation rate for C—SnS$_2$(C) is almost 124 times higher than the commercial SnS$_2$.

It's well accepted that the photocatalytic CO$_2$ reduction is a multi-electron reduction. In an initial step, direct photon absorption by the band gap of SnS$_2$ and generate electron-hole pairs. Therefore, the position of frontier orbital's of CO$_2$ with respect to the conduction band position SnS$_2$ would feasible for reduction process. Specifically, the narrow bandgap (around 2.5 eV) and the conduction band position with respect to onset reduction potential energy of CO$_2$ favoring for ten-electron reduction on the surface of photocatalyst. The ten-electron reduction processes are involved in the production of acetaldehyde in our experiment. On the other hand the excess polysulfide act as a sacrificial agent by hole scavenging to oxidize to elemental sulfur and suppress the corrosion of SnS$_2$. The overall reactions can be described in the following equations.

$$SnS_2 + h\nu \rightarrow SnS_2(e^- + h^+) \quad (1)$$

$$H_2O + 2h^+ \rightarrow 2H^+ + 1/2 O_2 \quad (2)$$

$$H_2O + h^+ \rightarrow 1/2 H_2O_2 + H^+ \quad (3)$$

$$H_2O + h^+ \rightarrow OH + H^+ \quad (4)$$

$$S^{2-} + 2h^+ \rightarrow S \quad (5)$$

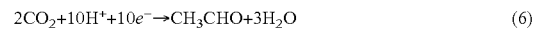
$$2CO_2 + 10H^+ + 10e^- \rightarrow CH_3CHO + 3H_2O \quad (6)$$

Although such properties demonstrated for in situ carbon doped SnS$_2$ nanostructures photocatalyst in these examples, other SnS$_2$ based hybrid photocatalyst according to the invention can be prepared and tested accordingly to the present disclosure and would exhibit similar catalytic activity.

Figure 12:
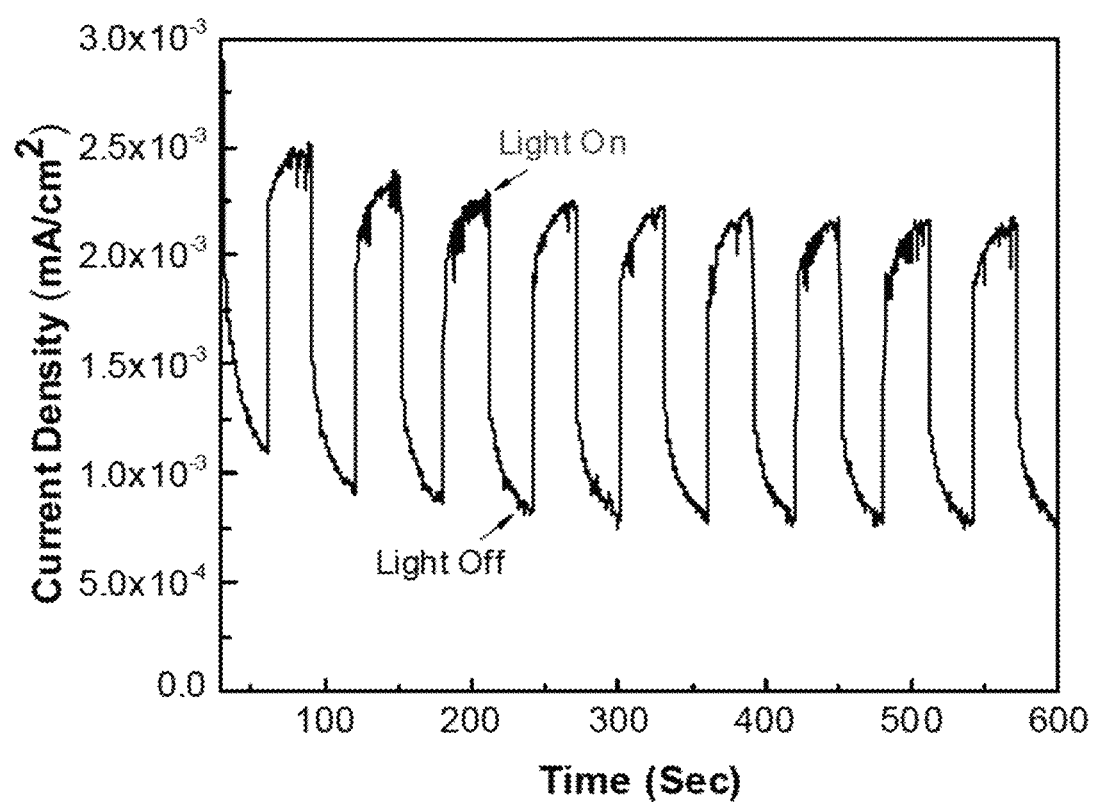
FIG. 12 On/off photocurrent response of C—SnS$_2$(C) at the external bias of 0.8V under 0.5M Na$_2$SO$_4$ electrolyte.

On the other hand, splitting of water to produce hydrogen and oxygen utilizing C—SnS$_2$(C) has been verified. As shown in FIG. 12, the on/off photocurrent response of C—SnS$_2$(C) at the external bias of 0.8V under 0.5M Na$_2$SO$_4$ electrolyte shows clear evidence of redox reaction under the light illumination. Despite the fact that additional separation of hydrogen and oxygen is needed to take advantage of this technique, proof of concept utilizing the abovementioned catalysts showed the potential for such application.

It will be appreciated by those skilled in the art of the changes could be made to the embodiments described above without departing from the broad invention concept thereof. It is understood, therefore, that this invention is not limited to the particular embodiments disclosed, but it is intended to cover modification within the spirit and scope of the present invention as defined by the appended claims.

OTHER PUBLICATION

Craig A. Grimes et al. Titania nanotubes arrays, methods of manufacture, and photocatalytic conversion of carbon dioxide using same, US20100213046A1 (2010)

Paul O'connor et al. Artificial photosysnthesis, WO2011020825A1 (2011)

Paul O'connor et al. Direct photoconversion of carbon dioxide to liquid products, WO2012168355A1 (2012)

Sun Yuanyuan et al. Visible light photocatalytic reduction of carbon dioxide over SnS$_2$, Materials Letters 174, 238-241 (2016).

What is claimed is:

1. A photocatalyst, comprising
a carbon doped tin sulfide, which is represented by formula I

$$C\text{—}SnS_x \quad (I),$$

wherein $1.5 \leq x \leq 2$.

2. The photocatalyst of claim 1, having a nanostructure which is selected from the group consisting of sheet type, flower type, sphere type, needle shape and a mixture thereof.

3. The photocatalyst of claim 2, having a nanostructure with a dimension ranging from 3 to 300 nm in length and in diameter.

4. The photocatalyst of claim 1, further comprising
a co-catalyst which is selected from the group consisting of metal, metal oxide, and metal sulfide and a mixture thereof, and
wherein the co-catalyst is deposited on the carbon doped tin sulfide.

5. The photocatalyst of claim 4, wherein the co-catalyst is selected from the group consisting of Ag, Cu, Au, Pt, Ni, Zn, $TiO_2$, ZnO, $WO_3$, $Cu_2O$, CuO, $SnO_2$, CdS, $MoS_2$, ZnS, NiS and a mixture thereof.

6. The photocatalyst of claim 1, wherein contents of Sn, S and C are 29.49-37.23, 55.32-57.69 and 7.45-12.82 atomic %, respectively.

7. The photocatalyst of claim 6, wherein the photocatalyst is $SnS_{1.95}C_{0.43}$ or $SnS_{1.49}C_{0.2}$.

8. The photocatalyst of claim 1, wherein the carbon doped tin sulfide is carbon doped tin disulphide ($C\text{—}SnS_2$) which is in a size of nanometer scale, and the photocatalyst has a sheet structure.

9. The photocatalyst of claim 8, wherein the carbon doped tin disulphide has a size of 3-300 nm.

10. The photocatalyst of claim 8, wherein the carbon doped tin disulphide has a carbon content ranging from 0.5% to 20%.

* * * * *